United States Patent [19]

Choi

[11] 4,282,201

[45] Aug. 4, 1981

[54] PHARMACEUTICAL COMPRISING DRUG AND POLYMER

[75] Inventor: Nam S. Choi, Seoul, Rep. of Korea

[73] Assignee: ALZA Corporation, Palo Alto, Calif.

[21] Appl. No.: 91,172

[22] Filed: Nov. 5, 1979

Related U.S. Application Data

[62] Division of Ser. No. 8,479, Feb. 2, 1979.

[51] Int. Cl.³ ............... A61K 9/22; A61K 9/24; A61K 9/26
[52] U.S. Cl. ............... 424/14; 424/16; 424/19; 424/22; 128/260
[58] Field of Search ............... 128/260; 424/14, 16, 424/19, 22

[56] References Cited

U.S. PATENT DOCUMENTS

| | | | |
|---|---|---|---|
| 4,066,747 | 1/1978 | Capozza | 424/78 |
| 4,070,347 | 1/1978 | Schmitt | 260/77.5 |
| 4,093,709 | 6/1978 | Choi et al. | 424/19 |
| 4,119,579 | 10/1978 | Capozza | 526/270 |
| 4,122,158 | 10/1978 | Schmitt | 424/27 |
| 4,131,648 | 12/1978 | Choi et al. | 424/22 |
| 4,136,252 | 1/1979 | Capozza | 528/403 |
| 4,138,344 | 2/1979 | Choi et al. | 252/1 |
| 4,155,740 | 5/1979 | Capozza | 71/28 |
| 4,155,992 | 5/1979 | Schmitt | 424/19 |
| 4,180,646 | 12/1979 | Choi et al. | 528/153 |
| 4,186,185 | 1/1980 | Capozza | 424/19 |

*Primary Examiner*—Shep K. Rose
*Attorney, Agent, or Firm*—Paul L. Sabatine; Edward L. Mandell; Thomas E. Ciotti

[57] ABSTRACT

This invention concerns polymers of the general formula:

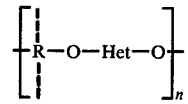

wherein R is a multivalent hydrocarbon radical and Het is a 5 to 8 membered heterocyclic system having a nitrogen, oxygen or sulfur hetero atom. The polymers are useful for making articles of manufacture and as coating for delivering beneficial agents.

5 Claims, 2 Drawing Figures

PHARMACEUTICAL COMPRISING DRUG AND POLYMER

CROSS REFERENCE TO RELATED APPLICATION

This application is a division of U.S. patent application Ser. No. 8,479 filed on Feb. 2, 1979, which is incorporated herein by reference and benefit is claimed of its filing date.

FIELD OF THE INVENTION

The present invention relates to polymers. More particularly, the invention pertains to both novel and useful polymers comprising a carbon-dioxygen backbone having a heterocyclic system bivalently bonded through a hetero carbon atom to the dioxygen atoms. The polymers are represented by the following general formula:

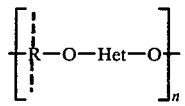

wherein (I) O is a divalent oxygen atom in the polymeric chain; (II), R is a di, tri or tetravalent hydrocarbyl; including alkylene; alkenylene; cycloalkylene; cycloalkylene substituted with alkyl, alkenyl, alkoxy, alkylene, and alkenylene; cycloalkenylene; cycloalkenylene substituted with an alkyl, alkenyl, alkoxy, alkylene or alkenylene; arylene; and arylene substituted with an alkyl, alkenyl, alkoxy, alkylene or alkenylene; and (III) Het is a monocyclic, heterocyclic five to eight membered ring comprising (1) a carbon atom bivalently bonded to the oxygen atoms of the polymeric chain; (2) a hetero ring atom pendant from and adjacent to the carbon atom bonded to the oxygen atoms in the polymeric chain, said hetero pendant atom selected from the group consisting of nitrogen, sulfur and oxygen; and (3) a bridge-forming member selected from the group consisting of an alkylene bridge and a hetero alkylene bridge that completes the remainder of the heterocyclic ring, the bridges independently selected from (a), (b), (c) and (d); wherein (a) is an alkylene bridge of 3 to 6 carbon atoms when the hetero pendant atom in (2) is a member selected from the group consisting of nitrogen and sulfur; (b) a hetero-alkylene bridge of 2 to 5 carbon atoms substituted with a hetero ring-forming member selected from the group consisting of nitrogen and sulfur when the hetero pendant atom in (2) is selected from the group consisting of nitrogen, oxygen and sulfur; (c) a hetero-dialkylene bridge of 2 to 5 carbon atoms substituted with a hetero ring-forming oxygen atom positioned between the dialkylene groups when the hetero pendant atom in (2) is selected from the group consisting of nitrogen and sulfur; and (d) an alkylene bridge of 3 to 6 carbon atoms substituted with an external group selected from amino alkyl substituted amino, and mercapto when the hetero pendant atom in (2) is a member selected from the group consisting of nitrogen, sulfur and oxygen. The generic formula also embraces, in addition to homopolymers, copolymers of the random and block type formed by reacting monomers or mixtures of preformed homopolymers and/or copolymers, branched polymers and cross-linked polymers. In the above formula n is greater than 10, usually 10 to 100,000.

DESCRIPTION OF PRIOR ART

The prior art teaches the reaction of orthoesters with glycols leading to non-polymeric and other diverse products in *Ind. J. Appl. Chem.*, Vol. 28, No. 2, pages 53 to 58, 1965 by Mehrota, et al. This reference also teaches that Mehrota, et al obtained monoethoxy-monoglycolate and triglycoxy-bisorthoformate by reacting orthoformate with hexamethylene glycol in molar ratios of one to one, and two to three to yield low molecular weight compounds. Similarly, Crank, et al in *Aust. J. Chem.*, Vol. 17, pages 1392 to 1394, 1964 discloses the reaction of triols with orthoesters including ethyl orthoformate with butane-1,2,4-triol, pentane-1,2,5-triol, and pentane-1,3,5-triol to form monomeric bicyclic compounds. During the preparation of the bicyclic orthoesters by reacting ethyl orthoformate with triols, Crank, et al found that compounds produced from starting materials having a 1,2,-diol structure also contained compounds having ethylene linkages. In a subsequent paper, Crank, et al *Aust. J. Chem.*, Vol. 17, pages 1934 to 1938, 1964, developed this reaction into a synthetic procedure for the conversion of 1,2,-diols into olefins. Later, DeWolfe in *Carboxylic Othro Acid Derivatives*, 1970, published by Academic Press, Inc., New York, noted that carboxylic orthoesters are more reactive toward acid hydrolysis than almost any other class of compounds, and this high hydrolytic reactivity complicates their synthesis and storage. DeWolfe reported the conversion of diols to cyclic orthoesters including alkoxydioxolane or alkoxydioxane, followed by acid hydrolysis, provided a method for monoacylating diols.

More recently, Bailey reported in *Polym Prepr. Amer. Chem. Soc. Div. Polym. Chem.*, Vol. 13, No. 1, pages 281 to 286, 1972, that the polymerization of spiro orthoesters at ambient and elevated temperatures led to polyesters and polycarbonates of structure $-[CH_2CH_2CH_2COOCH_2CH]_n-$ and $-[OCH_2OCOOCH_2CH_2CH_2]_n-$. The prior art as exemplified by British Pat. No. 1,239,504 discloses polyorthocarbonates synthesized by the reaction of a dihalodiaryloxymethane with a dihydroxy compound and a hydrogen halide acceptor. The polyorthocarbonates have the structure of a methanetetraol ether (carbonic acid orthoester) in the main chain. The patent is free of any suggestion of polymeric orthoesters and polymeric orthocarbonates having a hetercyclic ring, or a fused polycyclic ring functionality. The polymers of the patent are used for electrical insulation and lubricants for metal friction. The subject matter of British Pat. No. 1,239,504 also appears in French Pat. No. 1,601,220, and in *J. Polym. Sci.*, Vol. 10, pages 3518; 1972. Other orthoesters are disclosed in French Pat. No. 1,539,984 wherein the esters are prepared by treating suitable nitriles with hydrogen chloride to form imino ester hydrochlorides which are alcoholized to form the corresponding orthoesters. The patent does not disclose polymeric products having the present structure. In U.S. parent patent application Ser. No. 544,808 filed on Jan. 28, 1975, and now U.S. Pat. No. 4,093,709 issued on June 6, 1978, and in its divisional application, U.S. patent application Ser. No. 883,123 filed on Mar. 3, 1978, which applications are assigned to the same assignee as this application, inventors N. Choi and J. Heller disclosed orthoester and orthocarbonate polymers. The polymers of Choi and Heller comprise a polymeric backbone having a dioxycarbon unit with a multiplicity of hydrocarbon groups, or a heterocyclic mono- or di-oxa ring bonded thereto. The heterocyclic ring of the prior art is free of aza and thia members, and substituents containing a nitrogen or sulfur atom.

SUMMARY OF THE INVENTION

This invention concerns a novel and useful polymer. The polymer comprises a backbone containing a repeating unit which unit consists essentially of (a) and (b) wherein: (a) is a repeating dioxycarbon moiety covalently bonded to a monocyclic, heterocyclic ring comprising a carbon atom having a nitrogen, sulfur or oxygen atom bonded thereto with the proviso that when the ring atom is oxygen the ring also has an internal nitrogen or sulfur atom, or an external amino or mercapto group, and the carbon atom is positioned between and covalently bonded to the dioxycarbon moiety; and (b) is a polymeric chain-forming hydrocarbon radical bonded to one of the oxygens of the dioxycarbon backbone and it is a member selected from the group consisting of saturated or unsaturated, branched or unbranched acyclic radicals, and monocyclic unsubstituted and substituted aliphatic and aromatic rings. The polymers can be synthesized by conventional techniques. The polymers can be made into assorted articles of manufacture having various shapes, structures and sizes adapted for many environments of use. The polymer can also be used as coating for the controlled release of useful agents.

DETAILED DESCRIPTION OF THE INVENTION

Figure 1:
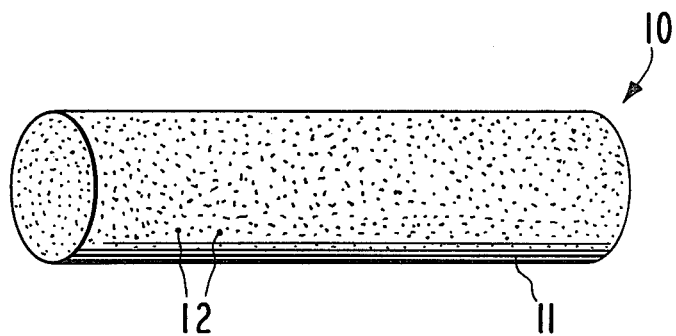

The phases hydrocarbon and hydrocarbyl as appearing above, and as used elsewhere in this specification, includes for the purpose of this invention, the divalent, trivalent and tetravalent radicals defined as follows:

The term alkyl as used herein denotes an alkyl group of 1 to 7 carbon atom, straight or branched, such as methyl; ethyl; n-propyl; n-butyl; n-amyl; n-hexyl; n-heptyl; and the various positional isomers thereof such as isopropyl; t-butyl; sec-butyl; isoamyl; isohexyl; t-heptyl; and the like.

The term alkenyl, as used herein includes straight and branched lower alkenyl groups of 2 to 7 carbon atom. Exemplary alkenyls include 1-propenyl; 2-propenyl; 1-butenyl; 2-butenyl; 1-pentenyl; 2-ethenyl; and the corresponding positional isomers such as 1-isobutenyl; 2-isobutenyl; 2-sec-butenyl; 2-methyl-1-butenyl; 2-methyl-2-pentenyl; 4,5-dimethyl-2-pentenyl; and the like.

The term alkoxy includes the straight and branched, and the positional isomers having 1 to 7 carbons, for example methoxy; ethoxy; propoxy; n-butoxy; n-pentoxy; n-hexoxy; isopropoxy; 2-butoxy; 3-pentoxy; and the like.

The term alkylene as used for this invention denotes a straight or branched chain alkylene of 1 to 10 carbons atoms inclusive, such as, methylene; 1,2-ethylene; 1,3-propylene; 1,4-butylene; 1,5-pentylene; 1,6-hexylene; 1,7-heptylene; 2-methyl-1,7-heplytene; 1,8-octylene; 1,10-decylene; 2-propyl-1,6-hexylene; 1,1-dimethyl-1,6-hexylene; and the like.

The term alkenylene denotes an unsaturated straight or branched chain multivalent radical having 2 to 10 carbon atoms such as 1,4-but-2-enylene; 1,6-hex-3-enylene; 1,7-hept-3-enylene; 1,8-oct-3-enylene; 1,5-pent-3-enylene; 1,9-non-3-enylene; 4-propyl-1,6-hex-3-enylene; 5-methoxy-1,6-hex-3-enylene; 2-propenyl-1,6-hex-3-enylene; and the like.

The term cycloalkylene includes saturated, monocyclic hydrocarbon radicals of 3 to 7 carbon atoms, such as cyclopropylene; cyclobutylene; cyclopentylene; cyclohexylene; and cycloheptylene. Similarly, the term cycloalkenylene includes monocyclic radicals having from 4 to 7 carbon atoms such as 1,4-cyclopent-2-enylene; 1,5-cyclopent-3-enylene; 1,6-cyclohex-2-enylene; and 1,4-cyclohex-2-enylene.

The phrase "cycloalkylene substituted with" includes cycloalkylenes of 3 to 7 carbons substituted with an alkyl of 1 to 7 carbons, an alkenyl of 2 to 7 carbons, and alkoxy of 1 to 7 carbons, an alkylene of 1 to 10 carbons, and an alkenylene of 2 to 10 carbons, as above-defined, and further exemplified by 2-methyl-1,3-cyclopropylene; 2-methyl-1,4-cyclopentylene; 2-ethoxy-2,3-cyclopropylene; 2-methoxy-1,4-cyclohexylene; 2-propenyl-1,5-cyclopentylene; 1-ethylene-4-cyclohexylene; 1,4-dimethylene-cyclohexylene; and the like.

The phrase "cycloalkenylene substituted with" includes cycloalkenylenes of 4 to 7 carbon atoms substituted with an alkyl of 1 to 7 carbons, an alkenyl of 2 to 7 carbons, an alkoxy of 1 to 7 carbons, an alkylene of 1 to 10 carbons and an alkenylene of 2 to 10 carbons, which terms are abovedefined, and further exemplified by, 5-methyl-1,4-cyclopent-2-enylene; 6-ethyl-1,4-cyclohex-2-enylene; 6-ethoxy-1,5-cyclohex-2-enylene; 2-propenyl-1,5-cyclohex-3-enylene; 2-methylene-1,4-cyclohex-2-enylene; 1,4-dimethylene cyclohex-5-enylene; 2-methoxy-1,4-cyclohept-2-enylene; and the like.

The terms arylene, and arylene substituted with an alkyl of 1 to 7 carbons, an alkenyl of 2 to 7 carbons, an alkoxy of 1 to 7 carbons, an alkylene of 1 to 10 carbons, and an alkenylene of 2 to 10 including the unsubstituted and substituted benzenoid group of 6 to 16 carbon atoms. Typical groups include phenylene, phenylalkylene, phenylalkenylene, 1,4-phenylene, 1,4-phenyldimethylene, 1,4-phenyldiethylene; 1-methylene-4-phenylene, 2-ethyl-1,4-phenyldimethylene, 2-methoxy-1,4-phenyldimethylene, 2-propenyl-1,4-phenyldiethylene; and the like.

The phrase hetero-alkylene bridge of 2 to 5 carbon atoms substituted with nitrogen or sulfur can be represented by moieties such as $-CH_2CH_2NH-$; $-CH_2CH_2CH_2NH-$; $-CH_2CH_2CH_2CH_2CH_2NH-$; $-CH_2CH_2NHCH_2CH_2-$; $-CH_2CH_2CH_2S-$; $-CH_2CH_2CH_2SCH_2-$; $-CH_2CH_2CH_2CH_2CH_2S-$; and the like. The phrase dialkylene bridge of 2 to 5 carbon atoms substituted with an oxygen atom positioned between the dialkylene group includes linear ethers such as $-CH_2CH_2OCH_2-$; $-CH_2CH_2OCH_2CH_2CH_2-$; and the like. The phrase an alkylene bridge of 3 to 6 carbon atom substituted with an external mercapto or amino group include those groups bonded to the ring-forming bridge, with the proviso the groups are not part of the ring, such as $-CH_2CH_2CH(NH_2)CH_2-$; $-CH_2CH_2CH(SH)CH_2CH-$; and the like. The amino group can be substituted with $CH_3$ groups.

The abbreviation "Het" as used for the purpose of this invention refers to a monocyclic, heterocyclic five to eight membered ring. The heteroatom ring is a component of the polymeric backbone. The ring is an integral constituent through a ring carbon atom that is positioned between and covalently bonded to the oxygen atoms of the backbone of the polymer. The ring has an annular, or internal ring-forming nitrogen, oxygen or sulfur atom pendant and covalently bonded to the ring carbon that is bonded to the backbone. The heterocyclic system is completed to form a five to eight membered ring containing one heteroatom, or a five to eight membered ring containing two heteroatoms by independently selecting the remainder of the ring from (a), (b), (c), or (d) wherein (a) is a hetero-alkylene bridge of 2 to 5 carbon atoms substituted with a ring-forming atom selected from the group consisting of nitrogen and sulfur; (b) is an alkylene bridge of 3 to 6 carbon atoms substituted with a nonring-forming member selected from the group consisting essentially of mercapto and amino; (c) is an alkylene bridge of 3 to 6 carbon atoms when the heteroatom of the adjacent and pendant to the ring carbon atom bonded to the oxygen atom in the polymeric backbone is a ring-forming member selected from the group consisting of nitrogen and sulfur; and (d) is a dialkylene bridge having an ether functionality positioned between alkylene members of the dialkylene bridge.

The novel polymers of the invention are synthesized by intimately contacting and reacting at least one starting difunctional polyol reactant mer, with at least one starting difunctional heterocyclic reactant mer to yield the corresponding polymers.

Exemplary polyols suitable as reactant mers include diols, triols and the like that can enter into the polymerization reaction without adversely effecting it or the polymeric product. The polyols are known to the prior art in reported systhesis, and they are commercially available. Generally, the polyols include acyclic diols, triols and the like of straight or branched, saturated or unsaturated hydrocarbon type; monocyclic diols, triols and the like of the unsubstituted or substituted, unsaturated or saturated hydrocarbon type; and moncyclic aromatic diols, triols and the like, of the unsubstituted or substituted aromatic hydrocarbon type.

Typical polyols include diols, named as the glycol, such as 1,5-pentylene glycol; 1,6-hexylene glycol; 1,7-heptylene glycol; 1,9-nonylene glycol; 2,3-dimethyl-1,6-hexylene glycol; 3,6-diethyl-1,9-nonylene glycol; 2-methoxy-1,4-butylene glycol; 1,5-pent-2-enylene glycol; 4-propyl-1,6-hex-3-enylene glycol; 1,4-but-2-enylene glycol; 4-methoxy-1,5-pent-2-enylene glycol; and the like.

Representative polyols containing more than 2 reactive hydroxyl radicals for use herein include polyhydroxyl compounds such as 1,2,3,4,5,6-hexanehexol; 1,2,3,-propanetriol; 1,2,5-pentanetriol; 1,3,5-pentanetriol; 1,2,4-butanetriol; 2-methyl-1,2,3-propanetriol; 2-methyl-2(hydromethyl)1,2-propanediol; 1,4,7-heptanetriol; 1,5,10-decanetriol; and the like.

Other polyols that can be used in accordance with the invention are polyhydroxyl compounds having 2 or more reactive hydroxyl groups such as 1,4-cyclohexane dicarbinol in the cis, trans isomeric configuration and mixtures thereof; 2,2,4,4-tetramethyl-cyclobutane 1,3-diol; 2-methoxy-1,4-cyclohexane dimethanol; 3-methyl-1,4-cyclopentane dicarbinol; 3,5-cyclohexane diethanol; 2,5-dipropyl-1,4-phenyldipropanol; 1,3-cyclopropanendiol; 2-propenyl-1,4-cyclohexane dipropanol; 1,4-cyclohex-3-ene dicarbinol; 2-methyl-1,4-cyclohexane diisopropanol; 3-isopropoxy-1,4-cyclohexane dipropanol; 2-isopropoxy-1,4-phenyldimethanol; 2-ethenyl-1,3-cyclopentane dicarbinol; 1,4-phenyldicarbinol; 2-propyl-1,4-phenyldiethanol; 3-butoxy-1,4-phenyldibutanol; and the like. The preparation of polyols is known to the art in Acta Pharm. Jugaslav., Vol. 2, pages 134 to 139, 1952; Justus Liebigs Ann. Chem., Vol. 594, pages 76 to 88, 1955; J. Am. Chem. Soc., Vol. 71, pages 3618 to 3621, 1949, ibid., Vol. 74, pages 2674 to 2675, 1952; Chem. Abst., Vol. 42, pages 8774 to 8775, 1948, ibid., Vol. 43, pages 571 to 573 and 6652, 1949, ibid., Vol. 44, pages 2554 and 7231, 1950, ibid., Vol. 46, page 9585, 1952, ibid., Vol. 47, page 7575, 1953, ibid., Vol. 48, page 106; 1954, ibid., Vol. 49, pages 6098 to 6099, 1955; Encyclopedia of Chemical Technology, Kirk-Othmer, Vol. 10, pages 638 to 678, 1966, published by Interscience Publishers, New York; and the references cited therein.

Exemplary starting heterocyclic monomers leading to the corresponding "Het" constituent of the polymer include heterocyclic amide acetals, heterocyclic thio ester acetals, substituted heterocyclic orthoesters, and substituted heterocyclic carbonates. The starting monomers are known to the prior art and they can be prepared by known reactions. For example, N-methyl-pyrrolidone diethyl acetal, or N-methyl-2,2-diethoxy-pyrrolidone is prepared by ethylation of the lactam with triethyloxonium tetrafluoroborate followed by reaction of the resulting salt with sodium ethoxide. Pyrrolidone dimethyl acetal, or 2,2-dimethoxy-pyrrolidone, is prepared from the amide chloride and sodium methoxide, and from pyrrolidone-dimethyl sulfate addition complex and sodium methoxide, see, Chem. Ber., Vol. 101, 41, 1968; Chem Zentr., Vol. 133, 10275, 1962; and Chem. Ber., Vol. 89, 2060, 1956. Similarly, 2,2-diethoxy-thiolane is prepared by reacting 2-ethoxythieolenium tetrafluoroborate with sodium ethoxide, see, Chem. Ber., Vol. 89, 2060, 1956. See also, Organic Chemistry, "Carboxylic Ortho Acid Derivatives," by DeWolfe, Vol. 14, pages 360 and 431 to 432, 1970, published by Academic Press, New York.

Other reactants such as dialkoxyisoxazolidines and difunctional dialkenyloxyasoxazolidenes can be synthesized by reacting ketene acetals of the general formula $R_1R_2C=C(OR_5)$ with nitrones of the formula $R_3CH=N(O)R_4$ to yield difunctional mers, wherein $R_1$ is hydrogen, alkyl, nitro, amine, and mercapto; $R_2$ is the same or different than $R_1$; $R_3$ is hydrogen, alkyl or aryl; $R_4$ is hydrogen, alkyl, phenyl, amino, nitro and mercapto; and $R_5$ is alkyl or alkenyl. The procedure is described in Gazetta Chemica Italiana, Vol. 96, No. 4, pages 375 to 386, 1966.

Also, other reactants, such as oxathiazoles, can be prepared by reacting a nitrate oxide of the formula $R_6$—CNO with a thiocarbonyl of the formula $R_7$—C-S—$R_8$ to yield the defunctional mer, wherein $R_6$ is hydrogen, alkyl, nitro, amino or mercapto; and $R_7$ and $R_8$ are the same or different alkoxy, alkenyloxy or phenyloxy. The thiocarbonyls include thioketones, alkyl thiocarboxylates, thiocarbonates, dithiocarboxylates and dithiocarbonates. A procedure for preparing oxathiazoles is described in Angew Chem., Vol. 73, No. 19, pages 656 to 657, 1961.

Additional monomers having heterocyclic ring structure leading to the present polymers include the difunctional amino and mercapto substituted 1,3-dioxolanes; the 1,3-dioxanes; the 1,3-dioxepanes; the 1,3 dioxocanes; and the amino and mercapto difunctional tetrahydrofurans; the tetrahydropyran; the 1-oxepane; and the like. Representative of these monomers include such as 2,2-diethoxy-4-aminotetrahydrofuran; 2,2-diethoxy-5-amino-1-oxepane; 2,2-diethoxy-6-mercapto-1-oxecane; 2,2-diethoxy-4-mercapto-tetrahydrofuran; 2,2-dialkoxy-4-mercapto-1-oxepane; 2,2-dimethoxy-5-amino-1,3- dioxolane; 2,2-diethoxy-6-amino-1,3-dioxocane; 2,2-diethoxy-5--1,3-dioxepane; and the like.

Procedures adaptable for preparing amino and mercapto derivatives are described in *Chem. Abst.*, Vol. 66, 28363g, 1967, ibid., Vol. 68, 59559w, 68977h, 1968, ibid., Vol. 69, 35351s, 1968, ibid., Vol. 70, 19915u, 88220a, 1969, ibid. Vol. 71, 3276w, 1969, ibid., Vol. 72, 90265d, 1970, ibid., Vol. 73, 4694j, 1970, ibid., Vol. 74, 13407r, 141736j, 1971, ibid., Vol. 77, 88301x, 126406v, 139685k, 151187g, 1972, ibid., Vol. 78, 4034x, 111059f, 1973, ibid., Vol. 79, 66769v, 1973, ibid., Vol. 80, 36865b, 1974, ibid., Vol. 81, 63438s, 1974, ibid., Vol. 83, 193651h, 1975, ibid., Vol. 84, 17068k, 1976, and ibid., Vol. 85, 192483j, 1976.

The heterocyclic monomers used herein also can be prepared by synthesis described in *Ber.*, Vol. 16, pages 352 to 353, 1883, ibid., pages 1664 to 1665, 1883; *Gen. Chem., U.S.S.R.*, Vol. 8, pages 1361 to 1367, 1938; *J. Am. Chem. Soc.*, Vol. 54, pages 2964 to 2966, 1932; U.S. Pat. Nos. 2,409,699; 2,867,667; 3,323,925; and 3,546,188; British Pat. Nos. 853,405 and 1,099,559; *Synthetic Organic Chemistry*, Chapter 16, pages 542 to 545, 1953; published by John Wiley and Sons; *The Chemistry of the Aliphatic Orthoesters*, Chapter 2, pages 11 to 43, 1943, published by Reinhold Publishing Corp., *Encyclopedia of Chemical Technology*, Vol. 8, pages 365 to 383, 1965, published by Interscience Publishers, New York; *Recueil Trav. Chem. Pays. Bes.*, Vol. 88, pages 897 to 904, 1909; *J. Am. Chem. Soc.*, Vol. 64, pages 1825 to 1927, 1942; *Ind. Eng. Chem. Prod. Res. Develop.*, Vol. 10, No. 4, pages 425 to 428, 1971; *J. Am. Chem. Soc.*, Vol. 71, pages 40 to 46, 1949; *Ann. Chem.*, Vol. 675, page 141, 1964; *Angew Chem.*, Vol. 69, page 371, 1957; *J. Am. Chem. Soc.*, Vol. 76, pages 5736 to 5739, 1954, ibid., Vol. 77, pages 5601 to 5606, 1955; *Chem. Ber.*, Vol. 89, page 2060, 1956; *Aust. J. Chem.*, Vol. 17, pages 1385 to 1398, 1964; *Gazz Chem. Ital.*, Vol. 96, page 1164, 1966; *Chem. Commun.*, page 13, 1967; *Carboxylic Ortho Acid Derivatives*, Chapters 1, 6 and 7, 1970, published by Academic Press, New York; *Chem. Abst.*, Vol. 68, 49006z, 1968; Chem. Abst., Vol. 51, 10472, 1957; *Chem. Abst.*, Vol. 56, 14083, 1957.

The novel polymers of this invention can be synthesized by intimately contacting and reacting a polyol monomer with a difuntional acetal-type heterocyclic monomer to yield the corresponding polymer. Generally, the polymerization reaction is carried out by reacting stoichiometric amounts of the reactants, or an excess of polyol to yield the polymer. That is, the amount of each reactive monomer can be from about 0.5 to 2 moles of polyol to 1 mole of heterocyclic monomer.

The polymerization of the monomers is carried out in a reaction vessel equipped with a stirrer and vacuum attachment with continuous mixing of the monomers in the presence of catalyst. The polymerization comprises an initial transesterification reaction followed by a polycondensation reaction with the complete polymerization performed at a temperature of 50° C. to 240° C., and over a reaction time of 1 hour to 120 hours. The transesterification step of the reaction consists in mixing the monomers and catalysts, and while continuously stirring the monomers, the temperature is gradually raised to about 180° C. The transesterification reaction for most monomers, occurs at 70° C. to 180° C., over a 1 to 24 hour reaction period, and at a normal atmospheric pressure with continuous distillation of the alcohol. The polycondensation reaction is commenced by reducing the pressure to usually less than 1.0 mm of mercury, generally in the range of 0.10 to 0.00001 mm of mercury, and while maintaining the elevated temperature and reduced pressure, carrying out the polycondensation by continuously mixing and reacting the reactants for several hours, generally in the range of 12 to 120 hours, or longer, to yield the polymer.

The polymer is recovered under anhydrous conditions from the reaction vessel by conventional isolation and recovery techniques. For example, the polymer is recovered while hot by extracting or pouring, or the polymer is isolated after cooling by dissolving it in a dry organic solvent such as benzene, carbon tetrachloride, methylene chloride, dioxane, toluene or xylene, followed by the addition of an organic liquid in which the polymer is insoluble, or has limited solubility to precipitate the polymer. Organic liquids for this latter purpose include ether, hexane, pentane, petroleum ether, hexane-heptane mixtures, and the like. The polymer is isolated by filtering and drying under anhydrous conditions. Other methods for recovering the polymer include lyophilizing from a solvent.

Representative catalysts for performing the polymerization reaction are Lewis acids such as boron trifluoride etherate, boron trichloride, boron trifluoride, stannic oxychloride, phosphorous oxychloride, phosphorous pentachloride, calcium acetate, antimony oxide, antimony pentachloride, antimony pentafluoride, stannous octoate, stannic chloride, diethyl zinc, n-butyl lithium, and mixtures thereof. The catalysts also include Bronsted catalysts such as p-toluene sulfonic acid, polyphosphoric acid, cross-linked polystyrene sulfonic acid, acidic silica gel, and mixtures thereof. Other catalysts may include neutral or basic catalysts such as tetrabutyl titanate, and titanium sodium hydrogen hexabutoxide. The amounts of catalyst used in about one part of catalyst to about 450 to 550 parts, usually 500 parts of difunctional heterocyclic monomer. Smaller, or larger amounts can be used, such as 0.005% to about 2.0% based on the weight of the starting monomer.

The polymerization optionally can be carried out in the presence of an inert organic solvent that does not adversely affect the reaction, or the reaction can proceed in the absence of added solvent. In the latter reaction one of the reactants, for example, the polyol initially serves as the solvent. As polymerization proceeds, solvent by-product is removed from the reactions by conventional distillation, azeotropic distillation, or by distillation under vacuum. Suitable azeotropic solvents include toluene, benzene, m-xylene, cumene, pyridine, n-heptane, the like, and mixtures thereof.

The following examples are set forth as representative methods illustrative of the spirit of the present invention. These examples are not to be construed so as to limit the scope of the invention, as these and other functionally equivalent means will be readily apparent to those skilled in the subject art.

EXAMPLE 1

To 0.350 moles of anhydrous trans-1,4-cyclohexane dicarbinol and 0.05 grams of polyphosphoric acid in a commercially available polymerization reactor is added with constant stirring under an inert nitrogen environment and normal atmospheric pressure 0.350 moles of dry 2,2-diethoxypyrrolidone. Next, the mixture is heated to 110°–115° C. and held at this temperature for 1½ to 2 hours, with slow distillation of a liquid formed. Then, while maintaining the temperature, the pressure is gradually reduced to 0.001 mm of mercury, and at this reduced pressure the temperature is slowly increased to 180° C. The reaction is continued at this temperature for 24 hours. The polymer is isolated by extruding it from the reactor. The polymer has the following structure, where n is the degree of polymerization from 10 to 1000.

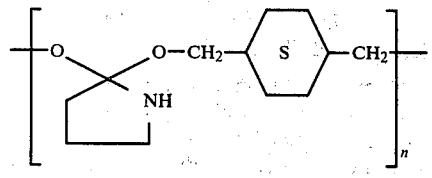

EXAMPLES 2-4

Following the procedure of Example 1, but replacing trans-1,4-cyclohexane dicarbinol and 2,2-diethoxypyrrolidone with:

trans-2-methyl-1,4-cyclohexane diethanol and 2,2-dimethoxypyrrolidone;

trans-2-methyl-1,4-cyclohexane dipropanol and 2,2-dimethoxypyrrolidone; and, trans-2-ethyl-1,4-cyclohexane dicarbinol and 2,2-diethoxy-N-methylpyrrolidone; and the following polymers are formed:

poly(2,2-dioxa-trans-2-methyl-cyclohexane-1,4-diethylene-2-pyrrolidone);

poly(2,2-dioxa-trans-2-methyl-cyclohexane-1,4-dipropylene-2-pyrrolidone); and poly(2,2-dioxa-trans-2-ethyl-cyclohexane-1,4-dimethylene-2-N-methyl-pyrrolidone).

EXAMPLES 5-6

Repeating the procedure of Example 1, but replacing the trans-1,4-cyclohexane dicarbinol with a member selected from the group consisting essentially of freshly distilled 1,6-hexanediol and 1,10-decanediol, the corresponding polymers of the following formula are obtained:

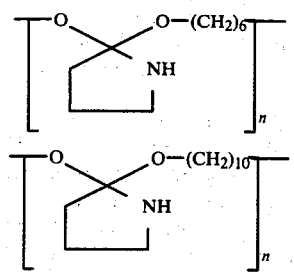

EXAMPLE 7

To 0.312 mole of dry trans, or cis/trans-1,4-cyclohexane dicarbinol and 0.05 grams of p-toluene sulfonic acid is added with constant agitation, 0.312 mole of 2,2-diethoxypiperidine and the polymerization reaction of Example 1 is repeated to yield the polymer shown below.

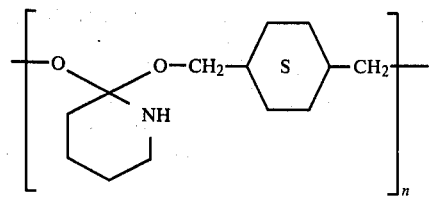

EXAMPLE 8

Repeating the procedure of Example 7, but replacing the trans, or cis/trans-1,4-cyclohexane dicarbinol with 1,4-phenyldimethanol, the following polymer is obtained.

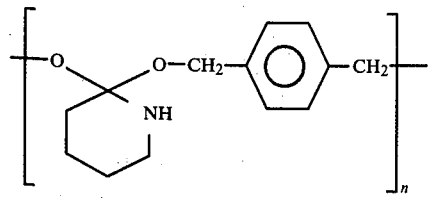

EXAMPLE 9

To a mixture of 0.375 mole of freshly distilled 1,6-hexanediol and 0.05 grams of polyphosphoric acid under a nitrogen blanket at atmospheric pressure is added with constant stirring 0.375 mole of 2,2-diethoxythiolane and the mixture heated to 110° to 120° C. The mixture is held at this temperature for 1.5 to 2.5 hours as ethanol slowly is distilled from the polymerization reactor. Next, the pressure is reduced to 0.01 mm Hg over a 2 hour period and at this vacuum the temperature is elevated to 180° C. over a similar 2 hour period. The reaction is allowed to continue for 24 hours to yield the polymer with the structure shown below, where n is 10 to 1000.

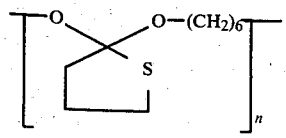

EXAMPLE 10-12

Repeating the procedure of Example 9, but replacing the 1,6-hexanediol and the 2,2-diethoxythiolane with stoichiometric reactive amounts of the following monomers:

cis,trans-1,4-cyclohexane dicarbinol and 2,2-diethoxythiane;

cis,trans-1,4-cyclohexane dicarbinol and 2,2-diethoxythiepane; and cis,trans-1,4-cyclohexane dicarbinol and 2,2-diethoxythiocane, the following polymers are obtained:

poly(2,2-dioxa-cis,trans-1,4-cyclohexane-dimethylene-2-thiane);

poly(2,2-dioxa-cis,trans-1,4-cyclohexane-dimethylene-2-thiepane); and, poly(2,2-dioxa-cis,trans-1,4-cyclohexane-dimethylene-2-thiocane).

EXAMPLE 13

To 0.312 mole of 1,10-decanediol and 0.05 grams of polyphosphoric acid in a reactor vessel, under a nitrogen environment and at atmospheric pressure, is added with constant stirring 0.312 mole of 2,2-diethoxy-4-dialkyl aminotetrahydrofuran. Next, the mixture is heated to 108°–115° C., and kept at this temperature for 1.5 to 2.5 hours as ethanol is gently distilled from the reactor. Then, while maintaining this temperature, the pressure is slowly reduced to 0.01 mm of mercury, and at this reduced pressure the temperature is raised to 180° C. The polycondensation is continued for 24 hours to yield the polymer with the structure shown below and with a degree of polymerization of 10 to 1000.

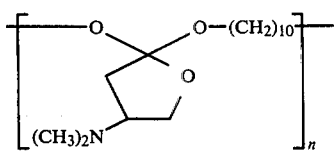

EXAMPLES 14–15

Repeating the procedure of Example 13, but replacing 1,10-decanediol and 2,2-diethoxy-4-amino-tetrahydrofuran with stoichiometric amounts of the following monomers:

1,6-hexanediol and 2,2-diethoxy-4-mercaptotetrahydrofuran; and
3-methyl-1,5-cyclopentanediethanol and 2,2-diethoxyoxy-4-amino-tetrahydrofuran, the following polymers are prepared:

poly(2,2-dioxahexamethylene-[4-mercapto-2-tetrahydrofuran]); and,
poly(2,2-dioxa-[3-methyl-cyclopentyl-1,5-diethylene]-[4-amino-2-tetrahydrofuran]).

EXAMPLE 16

The polycondensation of 2,2-diethoxyhexahydroazepine with 1,6-hexanediol in the presence of p-toluene sulfonic acid catalyst with the catalyst having a weight ratio of 1/500 to the 1,6-hexanediol, and the monomer ratio of about 2.2/1 of hexanediol to the diethoxyhexahydroazepine is carried out as follows: first, the hexanediol is introduced into a reactor and is mixed with freshly distilled toluene. Then, toluene is distilled in situ to azeotrope any water present from the system. Next, the diethoxyhexahydroazepine and the p-toluene sulfonic acid are added and transesterification and polycondensation are carried out at 175°–185° C., and at 1 millitor of vacuum over a 25 to 35 hour period to yield the polymer poly(2,2-dioxahexane-2-hexahydroazepine.).

EXAMPLES 17–21

In the instant examples, polymers are prepared according to the reaction procedure of Example 16. The polymers are prepared wherein the monomer pairs are as follows:

2,2-dialkoxy-octahydroazocine and 1,6-hexamethylene diol;
2,2-dialkoxy-diazepine and 1,4-phenylene dicarbinol;
2,2-dialkoxy-diazocine and 1,7-heptamethylene diol;
5,5-dialkoxy-1,2-oxathiolane and 1,6-hexamethylene diol; and,
2,2-dialkoxy-1,4-morpholine and 2-methyl-cis/trans-1,6-cyclohexanedipropanol; to yield the corresponding polymers:

poly(2,2-dioxahexamethylene-2-octa-hydroazocine);
poly(2,2-dioxa-1,4-phenyldimethylene-2-diazepine);
poly(2,2-dioxaheptamethylene-2-diazocine);
poly(2,2-dioxahexamethylene-1,2-oxathiolane); and,
poly(2,2-dioxa-[2-methyl-cis/trans-cyclohexyl-1,6-dipropylene]-[2-morpholine]).

DETAILED DESCRIPTION OF APPLICATION OF THE INVENTION

The polymers of the invention are useful for making articles of manufacture including devices, and coatings for releasing beneficial agents. The polymers can be processed into articles, including delivery devices and coated onto an agent by standard manufacturing techniques. For example, the polymers can be extruded into filaments, pressed into shaped articles, solvent film cast, doctor-bladed into thin films, coated onto an agent by solvent evaporation, compression and transfer molded, and processed by like standard methods of manufacture. Other devices provided by the invention include a device for the controlled release of an active agent wherein the device is a matrix of the polymer having an active agent present in the matrix with the device eroding and releasing agent over time.

The polymers of the invention can be used as a single film, or in a number of layers made of differet polymers of this invention, and they can be made into devices of various geometric shapes, for example, flat square, round, tubular, disc, ring and the like. Also, the devices of the invention are sized, shaped and adapted for implantation, insertion or placement on the body, in the body, its cavities and passageways, or for positioning in other environments for example, fields or reservoirs. The polymers are useful for making devices for dispensing an active agent and for use as coatings as they erode with an accompanying dispensing of the agent. Standard procedures for processing the polymers are described in *Plastic Encyclopedia*, Vol. 46, pages 62–70, 1969.

The terms "active agent," and "beneficial agent" as used in this specification and accompanying claims includes pesticides, herbicides, germicides, biocides, algicides, rodenticides, fungicides, insecticides, plant growth promoters, plant growth inhibitors, preservatives, disinfectants, sterilization agents, cosmetics, drugs, plant foods, fertilizers, vitamins, sex sterilants, plant hormones, fertility inhibitors, fertility promoters, air-purifiers, micro-organism attenuators, nutrients and the like.

The term drug as comprehended by the invention broadly includes a member selected from the group consisting essentially of local and systemic drugs that produce a physiologic and pharmacologic beneficial result in animals, avians, reptiles and pisces. The term animals includes mammals, and mammals include humans. Animals also include household, sport and farm animals such as sheep, goat, cow, dog, cat, etc. The drug that may be administered includes both inorganic and organic drugs of the local and systemic type that act on the nervous system, hypnotics, sedatives, narcotic antagonists, psychic energizers, tranquilizers, muscle relaxants, antiparkinson, analgesics, antipyretics, anti-inflammatory, anesthetics, antispasmodics, antiulcer, prostaglandins, anti-microbials, anti-malarials, antivirals, hormones, androgenic steroids, estrogenic steroids, progestational steroids, corticosteroids, sympathomimetic amines, cardiovascular drugs, diuretics, neoplastics, hypoglycemic, nutritional agents, vitamins, amino acids, essential elements, ophthalmic drugs, and the like. The above drugs and their present dose are further described in *The Pharmacological Basis of Therapeutics*, edited by Goodman and Gilman, 4th Edition, 1970, published by The Macmillan Company; *The Drug, the Nurse, the Patient*, by Falconer, Ezell, Patterson, and Gustafson, 1974, published by W. B. Saunders Co.; *Medical Pharmacology*, by Goth, 4th Edition, 1968, The C. V. Mosby Company; and *American Drug Index*, by Billups and Billups, 1978, published by J. B. Lippincott Co.

The agents can be in various forms, such as uncharged molecules, components of molecular complexes, salts, esters, ethers and amides which have solubility characteristics compatible with the polymer, are suitable for the purpose of this invention. Also, an agent that has limited solubility, or is water insoluble can be used in a form that is a water soluble derivative thereof to effectively serve as a solute, and on its release from the polymer, it is converted by the environment including enzymes, hydrolyzed by body pH, or metabolic processes to the original form or to an active form. Additionally, agent within the polymers can have various art known forms such as solution, dispersion, paste, cream, particles, granules, emulsions, suspension, powders, micronized powders, and the like.

The polymers are useful in a presently preferred embodiment for manufacturing polymeric delivery compositions containing a drug which composition erodes in an aqueous environment with an accompanying release of drug. For example, a composition is prepared by heating the polymer of Example 1 until it becomes pliable and then adding micronized hydrocortisone to the polymer. Next, the polymer and the hydrocortisone are thoroughly mixed to produce a good dispersion of the steroid, and to yield a 5% hydrocortisone loaded polymer. After the polymer drug formulation cools to room temperature, the formulation can be molded in a preselected design that is sized, shaped and adapted for positioning and placement in the biological environment of use. A formulation containing hydrocortisone can be used for the management of inflammation and bursitis when applied to a drug receptor site. In accompanying FIG. 1, a polymer drug formulation is seen sized, shaped and adapted as device 10 for delivering the drug to a local drug receptor site. Device 10 comprises the polymer 11 and drug 12 distributed therethrough. Generically, for this embodiment and other embodiments, the polymer agent formulation can contain from 0.001% to about 50% by weight of agent, including drug, with a presently preferred range of from 0.01% to about 40% by weight of agent.

Figure 2:
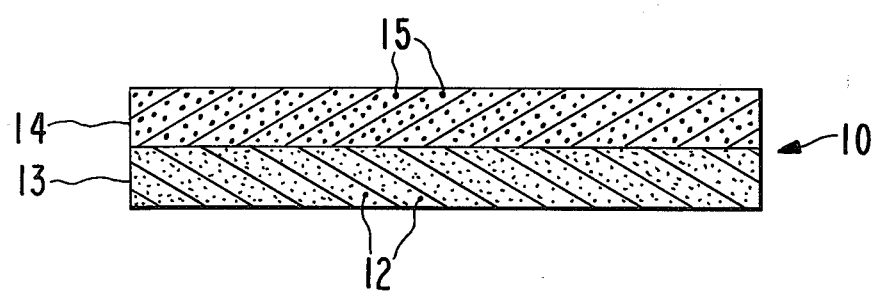

A bilayer film of two different polymers also can be used for delivering agents to an environment of use. The bilayer film, manufactured in the form of delivery device 10, is seen in FIG. 2. Device 10 comprises layer 13 in a laminar arrangement with layer 14, with each layer formed of a different polymer having a different erosion rate. An agent is dispersed in each layer, which agent 12 in layer 13 can be the same or different than agent 15 dispersed in layer 14. For example, the device can be used to deliver the juvenile hormones, such as methyl-10,11-(cis)osido-7-ethyl-3,11-dimethyl-trideca-2(trans),6(trans)dienoate in one layer, and the active agent 2,4-dichlorophenoxyacetic acid in the outer layer.

Many variations of device 10 will be apparent to those skilled in the art of dispensing agents in the light of this invention. For example, a greater number of layers can be used, a variety of agents, including drugs, can be used in several layers, and polymers having different erosion rates can be used for obtaining different delivery patterns.

In another embodiment, the polymers are useful for coating agents that lend themselves to use as slow release fertilizers. The fertilizers are coated in their conventional forms such as granules, powder, beads, particles, and the like. Fertilizers that can be coated include urea, fertilizers with slow ammonia release, fertilizers in the form of water soluble salts, which salts contain nitrogen, phosphorous, and sulfur, potassium, calcium, magnesium, manganese, zinc, copper, boron, and the like. Also, fertilizers such as the common fertilizers designated by 8-24-12, 8-8-6, 5-20-20, 12-12-12, 14-16-0, 8-4-6, 3-9-6, and the like. Additionally, the fertilizer or plant nutrient can be impregnated into, or suitably admixed with inert materials, such as silica, coke, and the like.

In one embodiment, the polymers prepared according to the spirit of the invention are applied to the fertilizers, for example, in granular form by mixing the fertilizer and the polymer in a fluidized bed having a conical bottom. The bed is equipped with an inert gas inlet at the top for introducing gas for mixing the polymer and the fertilizer until the fertilizer is coated with 0.1 to 10% by weight of polymer. The temperature of the gas is dependent on the concentration of the dispersion, usually 20° to 125° C. The conical device also can have exterior means for governing the temperature of the process. In another embodiment, the fertilizer is coated by mixing the polymer with an organic solvent to facilitate its application in thin coat form to the fertilizer granules. The selection of suitable solvents in view of those set forth above, is within the skill of the art. The coating compositions can additionally contain pigments, dyes, driers, stabilizers and the like.

It will be appreciated by those versed in the art, the present invention makes available novel polymers useful for making items of science and commerce, including devices for dispensing a beneficial agent. Also, it will be understood by those knowledgeable in the art, that many embodiments of this invention can be made without departing from the spirit of the invention, and the invention is not to be construed as limited, as it embraces all equivalents inherent herein.

I claim:

1. A drug delivery device for the administration of drug to a biological drug receptive environment, wherein the device comprises: (I) a shaped matrix sized, structured and adapted for administering drug to the environment and formed of a drug release rate controlling pharmaceutically acceptable material, which material comprises a polymer of the formula:

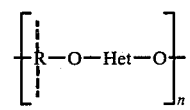

wherein R is a member selected from the group consisting of divalent, trivalent, and tetravalent radicals consisting of alkylene of 1 to 10 carbons; alkenylene of 2 to 10 carbons; cycloalkylene of 3 to 7 carbons; cycloalkylene 3 to 7 carbons substituted with an alkyl of 1 to 7 carbons, an alkenyl of 2 to 7 carbons, an alkoxy of 1 to 7 carbons, alkylene of 1 to 10 carbons, and alkylene of 2 to 10 carbons; cycloalkenylene of 4 to 7 carbons, cycloalkylene of 4 to 7 carbons substituted with an alkyl of 1 to 7 carbons, alkenyl of 2 to 7 carbons, alkoxy of 1 to 7 carbons, alkylene of 1 to 10 carbons and alkenylene of 2 to 10 carbons; arylene of 6 to 16 carbons; arylene of 6 to 16 carbons substituted with an alkyl of 1 to 7 carbons, alkenyl of 2 to 7 carbons, alkoxy of 1 to 7 carbons, alkylene of 1 to 10 carbons and alkenylene of 2 to 10 carbons; and Het is a heterocyclic five to eight membered ring comprising: (1) a carbon atom bivalently bonded to the oxygen atoms of the polymer; (2) a hetero ring atom adjacent to the carbon atom of the polymer chain, said hetero atom selected from the group consisting of nitrogen, sulfur and oxygen; and (3) with the remainder of the ring independently selected from (a) and (b) wherein (a) is an alkylene bridge of 2 to 5 carbons substituted with a ring atom selected from the group consisting of nitrogen and sulfur; and (b) is an alkylene bridge of 3 to 6 carbons when said hetero atom adjacent to the carbon atom of the polymer chain is a hetero ring atom selected from the group consisting of nitrogen and sulfur; and n is greater than 10; (II) a drug selected from the group consisting of locally and systemically acting physiologically and pharmaceutically acceptable drug present in the matrix; and (III) wherein the device when in operation administers a therapeutically effective amount of drug to the environment over a period of time.

2. The drug delivery device for the administration of drug according to claim 1 wherein the drug receptive environment is an animal.

3. The drug delivery device for the administration of drug according to claim 1 wherein the drug receptive environment is a human and the matrix contains from 0.01% to 40% by weight of drug.

4. The drug delivery device for the administration of drug according to claim 1, wherein the remainder of the heterocyclic ring comprises an alkylene bridge of 3 to 6 carbons substituted with an extralinear member selected from the group consisting of mercapto and amino.

5. The drug delivery device for the administration of drug according to claim 1, wherein the remainder of the heterocyclic ring is a dialkylene bridge of 2 to 5 carbon atoms having a linear ether between alkylene group of the bridge when the hetero atom pendant from the polymer backbone is selected from the group consisting of nitrogen and sulfur.

* * * * *